United States Patent [19]
Terauchi et al.

[11] Patent Number: 5,570,192
[45] Date of Patent: Oct. 29, 1996

[54] SAMPLE OPTICAL PROPERTIES MEASURING DEVICE WITH PREDICTIVE ESTIMATION OF MEASUREMENT RANGE BY USING PRELIMINARY AND MAIN LIGHT EMISSION

[75] Inventors: Koichi Terauchi, Toyohashi; Tomomi Ono, Akashi, both of Japan

[73] Assignee: Minolta Co., Ltd., Osaka, Japan

[21] Appl. No.: 300,971

[22] Filed: Sep. 6, 1994

[30] Foreign Application Priority Data

Sep. 6, 1993 [JP] Japan ..................... 5-220952

[51] Int. Cl.$^6$ ........................... G01N 21/25; G01J 3/46
[52] U.S. Cl. ..................... 356/407; 356/419; 356/425
[58] Field of Search ..................... 356/407, 416, 356/419, 425

[56] References Cited

U.S. PATENT DOCUMENTS

| | | | |
|---|---|---|---|
| 3,822,098 | 7/1974 | Rudder et al. | 356/407 |
| 4,029,419 | 6/1977 | Schumann, Jr. et al. | 356/419 |
| 4,131,367 | 12/1978 | French et al. | 356/425 |
| 4,620,097 | 10/1986 | Tanaka et al. | 250/327.2 |
| 4,773,761 | 9/1988 | Sugiyama et al. | 356/416 |
| 4,884,221 | 11/1989 | Sugiyama et al. | 356/407 |
| 4,886,366 | 12/1989 | Kogure | 356/425 |
| 4,989,982 | 2/1991 | Osaki et al. | 356/419 |
| 5,268,730 | 12/1993 | Takagi | 354/415 |

FOREIGN PATENT DOCUMENTS

| | | | |
|---|---|---|---|
| 0081702 | 6/1983 | European Pat. Off. | 356/416 |
| 52-031783 | 3/1977 | Japan | 356/419 |
| 58-103071 | 6/1983 | Japan | 356/407 |
| 03202731 | 9/1991 | Japan | 356/425 |

*Primary Examiner*—Frank Gonzalez
*Assistant Examiner*—Jason D. Eisenberg
*Attorney, Agent, or Firm*—Price, Gess & Ubell

[57] ABSTRACT

The optical properties measuring device of this invention performs preliminary emission of light from a light source prior to main light emission for sample measurement, and approximates the optical properties of the sample based on the output from a photosensor at the time of preliminary emission. Then, based on the approximated optical properties, the luminous energy for the main light emission for sample measurement is determined. Main light emission from the light source in accordance with the luminous energy determined this way is then performed, and the sample's optical properties are calculated based on the output at this time. In other words, this invention is characterized in that the sample's optical properties are approximated beforehand by means of this preliminary light emission, and the luminous energy at the time of the main light emission to perform sample measurement is changed in accordance with the result of this calculation. In this way, high-precision measurement of a sample may performed at all times regardless of the optical properties of the sample.

18 Claims, 5 Drawing Sheets

SAMPLE OPTICAL PROPERTIES MEASURING DEVICE WITH PREDICTIVE ESTIMATION OF MEASUREMENT RANGE BY USING PRELIMINARY AND MAIN LIGHT EMISSION

BACKGROUND OF THE INVENTION

1. Field of the Invention

This invention relates to a device that measures a sample's optical properties, such as spectral reflectance or spectral transmittance, and particularly to a device which can perform high-precision measurement at all times regardless of the optical properties of the sample.

2. Description of the Prior Art

Conventionally, a device that measures the optical properties of a source and receiving the light from the measurement sample is generally and widely known. One example is a colorimetric device that measures the color of a sample by receiving the light reflected off or passing through the sample. The prior art and this invention will be explained below with reference to a colorimetric device, and particularly to a device that performs color measurement of a sample by receiving the light reflected off a sample. An explanation of various devices that receive light passing through a sample will be omitted because, other than a construction that leads the light from the sample to a measuring member, their construction is identical with that of the above device. In addition, this invention may be easily applied in the construction of a device that measures the sample's density and other optical properties because the device's construction is almost the same.

In a device that receives reflected light from a sample and measures the color, the sample is first irradiated with a white light source, etc. and the reflected light is dispersed into multiple basic wavelength components using a spectral filter, etc. Each of the dispersed wavelength components is then received by a photoelectric conversion element such as a photodiode, and the electric current or voltage proportionate to the luminous energy of the light is output as a measurement value. Incidentally, the output from this photoreceptor element is generally converted from analog to digital form so that it may be processed by a digital CPU, etc.

Now, because the luminous energy of the light received by the photoreceptor element is indicated by the product of the luminous energy of the light emitted by the light source and the reflectance of the measurement sample, the count value, which is the output of the photoreceptor element after A/D conversion, is proportionate to the luminous energy of the light emitted by the light source and the reflectance of the sample. In other words, the relationship given below exists:

(count value)=k×(luminous energy of the light emitted by the light source)×(sample reflectance)    (1), where k is a proportional constant.

In addition, the resolving power per one count of count value is indicated by (resolving power)=(reflectance)/(count value)    (2)

In the conventional colorimetric device, when a sample having a relatively high reflectance, such as a white sample, is being measured, a photoreceptor element is selected so that the element output does not overflow, and an A/D conversion circuit constant is determined so that the circuit's counter does not overflow. For example, when designing a device such that the count value equals 10,000 when measuring a sample having 100% reflectance, the resolving power becomes (resolving power)=100%/10.000=0.01%    (3)

In other words, with this colorimetric device a reflectance up to a range of 0.01% can be measured.

Figure 6:
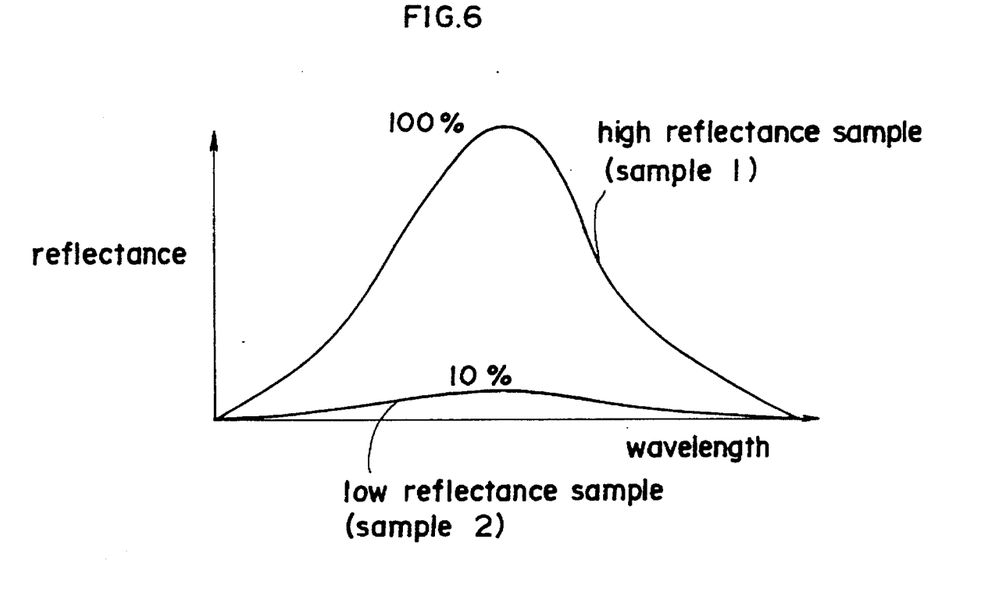
FIG. 6 is a graph showing the spectral reflectance of two types of measurement sample, i.e., high-reflectance and low-reflectance.

Next, a case where measurement of the two types of sample shown in FIG. 6 is performed using this colorimetric device will be considered. Sample 1 is a sample with a maximum reflectance of 100%, while sample 2 is a sample having a reflectance which is one-tenth of that of sample 1 for each wavelength. Since the high-reflectance sample 1 having a maximum reflectance of 100% can be measured up to a range of 0.01%, the ratio between the maximum measurable reflectance and the minimum measurable reflectance is 10.000:1. However, since the low-reflectance sample having a maximum reflectance of 10% can be measured only up to a range of 0.01%, the ratio between the maximum measurable reflectance and the minimum measurable reflectance is 1000:1.

When measuring the color of a substance, since color is distinguished by device of whether the relative relationships between the various dispersed wavelength components are large or small, the larger the ratio between the maximum measurable reflectance and the minimum measurable reflectance is, the better the capability to distinguish color is. However, when measuring sample 2 as described above, the above ratio with respect to sample 1 is 1:10. In other words, the ability of the colorimetric device to distinguish color when measuring low-reflectance sample 2 is one-tenth of that present when measuring high-reflectance sample 1.

Consequently, in the conventional colorimetric device, the lower the sample's reflectance is, the smaller the ratio becomes between the maximum measurable reflectance and the minimum measurable reflectance, and the problem arises that the colorimetric device becomes accordingly less able to distinguish color.

With a low-reflectance sample as well, the resolving power may be increased in order to perform precise color measurement, and the A/D conversion circuit count value may be increased in order to increase the resolving power. As methods to increase the count value, the luminous energy of the light emitted by the light source may be increased, as is understood from equation (1) above, or the number of bits or the gain of the A/D conversion circuit may be increased in order to increase proportional constant k. However, in the conventional colorimetric device the light source constantly performs emission of the maximum luminous energy. Furthermore, in connection with proportional constant k, when the number of bits in the A/D conversion circuit is increased, the price of the circuit increases proportionally, resulting in higher manufacturing costs. In addition, when the gain is increased and measurement of a low-reflectance sample is performed, the S/N ratio of the output signal falls, and errors increase. Moreover, it requires that the gain be alternated when a high-reflectance sample is measured and when a low-reflectance sample is measured.

The present invention takes the above problems into account, and its object is to provide an optical properties measuring device which is capable of measurement with high accuracy at all times regardless of the sample's optical properties, such as high or low reflectance.

SUMMARY OF THE INVENTION

The optical properties measuring device of this invention performs preliminary light emission from a light source prior to performing the main light emission to measure the sample, and the optical properties of the sample are approximated based on the output from the photosensor at the time of preliminary emission. The luminous energy of the light to be emitted during tile main emission for measurement of optical properties is then determined based on the approximated optical properties. The main light emission from the light source is then carried out in accordance with this determined luminous energy to be emitted, and the sample's optical properties are calculated based on the output at this time. In other words, the sample's optical properties are approximated beforehand by means of the preliminary light emission, and the luminous energy of the light to be emitted during the main light emission that performs measurement of optical properties is changed in response to the result of this calculation. In this way, the optical properties of the sample may always be measured with high accuracy regardless of the sample's optical properties.

Measurement of sample 1 and sample 2 described above by a measuring device that measures spectral reflectance applied in the present invention is considered below.

Regarding high-reflectance sample 1, first the sample's reflectance is calculated via the carrying out of preliminary light emission. Since it may be determined from this calculation that sample 1 has high reflectance, the light source is made to emit 10% of the luminous energy of the light (hereinafter referred to as '10% emission') it would emit during maximum emission. The circuit constant is then designed so that the count value for maximum reflectance at this then becomes 10,000 counts. In this case, where the luminous energy of the light emitted by the light source is indicated by $L(10)$, proportional constant k becomes as follows based on the above equation (1):

$$k = 10,000/\{L(10) \times 100\} \quad (4)$$
$$= 100/L(10)$$

The resolving power, based on equation (2) above, becomes $$\text{(resolving power)} = 100\% / 10,000 = 0.01\% \quad (5)$$

On the other hand, when sample 2 is measured as well, the reflectance is similarly sought by means of the preliminary light emission, and when it is determined that the reflectance is low, the light source emits the maximum (100% emission) luminous energy of the light. If the luminous energy emitted during 100% emission is deemed $L(100)$, the count value when sample 2 is measured becomes, according to equations (1) and (4).

$$\begin{aligned}\text{(count value)} &= k \times L(100) \times 10 \quad (6)\\ &= \{100/L(10)\} \times L(100) \times 10\\ &= 1000 \times L(100)/L(10)\\ &= 10,000.\end{aligned}$$

$$\text{(however, } L(100)/L(10) = 10)$$

The resolving power becomes, according to equation (2), $$\text{(resolving power)} = 10\%/10.000 = 0.001\% \quad (7)$$

As may be seen from equations (5) and (7), with the colorimetric device of this invention, measurement of high-reflectance sample 1 may be performed up to a range of 0.01%, while measurement of low-reflectance sample 2 may be performed up to a range of 0.001%. In other words, the resolving power when measuring sample 2 is ten times the resolving power when measuring sample 1. As a result, the ratio between the maximum measurable reflectance and the minimum measurable reflectance is 10,000:1 when either sample 1 or sample 2 is measured.

In this way, by changing the luminous energy emitted from the light source in accordance with the sample's reflectance, the problems with the conventional devices that the lower the reflectance of a sample is, the smaller the ratio between the maximum measurable reflectance and the minimum measurable reflectance is and that the ability to distinguish color falls, are solved in the colorimetric device in which this invention is applied.

Other objects and advantages of the present invention will become apparent from the detailed description to follow taken in conjunction with the appended claims.

DETAILED DESCRIPTION OF THE PREFERRED EMBODIMENTS

An embodiment of the present invention is described below with reference to the drawings.

Figure 1:
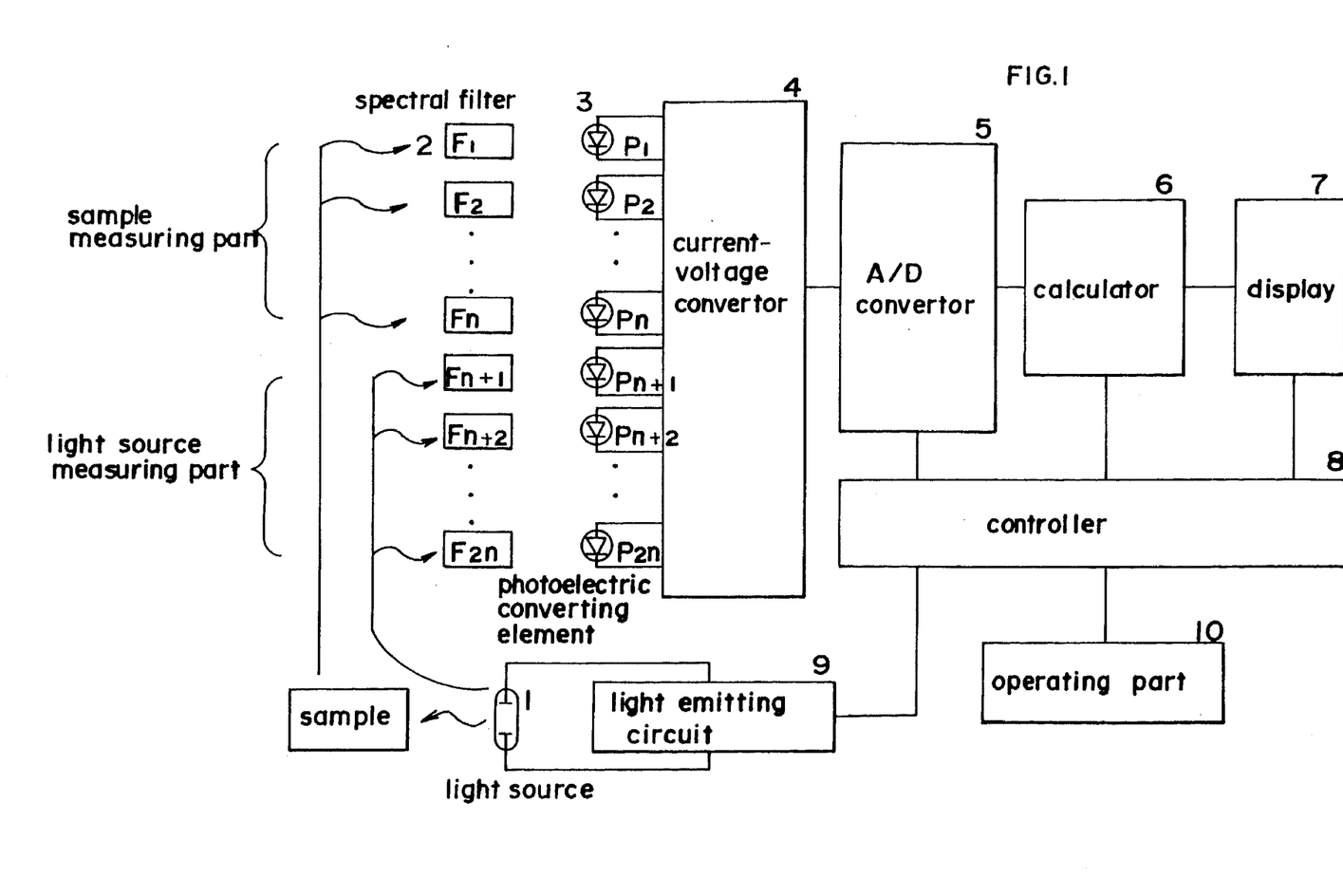
FIG. 1 is a block diagram showing the entire construction of the colorimetric device pertaining to one embodiment of the present invention.

FIG. 1 is a block diagram showing the entire construction of a spectral colorimeter that comprises one embodiment of the present invention. 1 is a light source for emitting light onto a sample, which employs a xenon flash lamp (hereinafter referred to as a 'xenon lamp') in this embodiment. The light emitted by light source 1 is reflected off the sample and dispersed into basic wavelength components by components (F1–Fn) of spectral filter 2. The dispersed beams of light of each wavelength component are received by components (P1–Pn) of photoelectric conversion element 3. On the other hand, components (Fn+1–F2n) of spectral filter 2 each have the same spectral properties as the above filter components (F1–Fn), and disperse the direct light from light source 1. Components (Pn+1–Pn) of photoelectric conversion element 3 receive the light dispersed by filter components (Fn+1–F2n). The output from these photoelectric conversion element components (Pn+1–P2n) is used in correcting for fluctuation of the light source, and by dividing this output into the output of photoelectric conversion element components (P1–Pn) that receive the light from the sample, standardization of the measurement value is carried out. As a result of this standardization, fluctuations in the measurement value may be avoided even where the light from the light source fluctuates.

The output from photoelectric conversion element 3 is converted to voltage values in accordance with the light intensity via current/voltage conversion circuit 4, and is then converted to digital count values (hereinafter referred to simply as 'count values') by A/D conversion circuit 5. Calculation unit 6 inputs the count values output from the A/D conversion circuit and indicating the light intensity of each basic wavelength component, and calculates the samples spectral reflectance. Each color specification value such as L*, a*, b*, etc. is then calculated from the calculated spectral reflectance, and is displayed by display 7.

Controller 8 is a controller that controls the operation of each block and the signal flow, and comprises, for example, a digital CPU. Light emitting circuit 9 is a circuit comprising a booster circuit and a trigger circuit, and causes the flash lamp, i.e., the light source, to emit light in response to the signal from controller 8. Operation member 10 is an operation member to allow the user to operate the colorimetric device.

Figure 2:
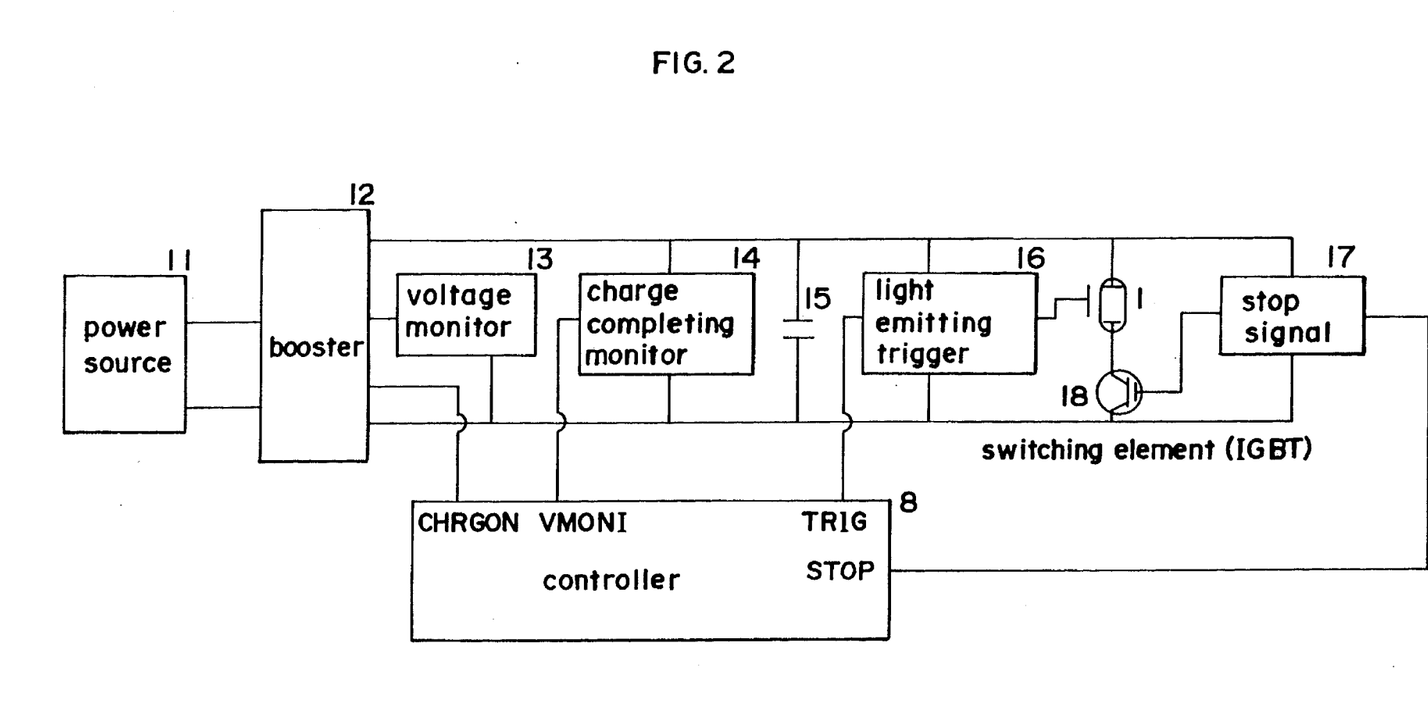
FIG. 2 is a block diagram showing the basic construction of the light emitting circuit.

FIG. 2 is a block diagram showing the basic construction of said light emitting circuit 9. 11 is a power source that supplies electric current to the circuit, and 12 is a booster circuit that boosts the voltage of power source 1 to the level necessary in order to cause light source 1 to emit light. 13 is a voltage detection circuit that detects the voltage boosted by booster circuit 12. 15 is a capacitor which is charged with the electric current output from the booster circuit, and light source 1 emits light by means of the strong electric current transmitted in a single discharge from capacitor 15. 14 is a charge completion monitoring circuit that monitors whether a charge having the voltage necessary to cause light source 1 to emit light has been stored. 16 is a trigger circuit to begin the emission of light from light source 1, and 17 is a circuit that outputs a signal to cause light source 1 to stop emitting light.

18 is a switching element to turn ON and OFF the emission of light from light source 1. Since a current exceeding one hundred amperes runs through this element when light source 1 emits light, it is required that this switching element 18 be able to operate with strong electric current. In addition, because it is necessary to stop the light emission in the midst thereof, the element must be able to respond quickly. In this embodiment, therefore, an IGBT semiconductor element is employed to quickly turn the supply of strong electric current to this switching element 18 ON and OFF. Incidentally, IGBT is an abbreviation for Insulated Gate Bipolar Transistor.

Figure 3:
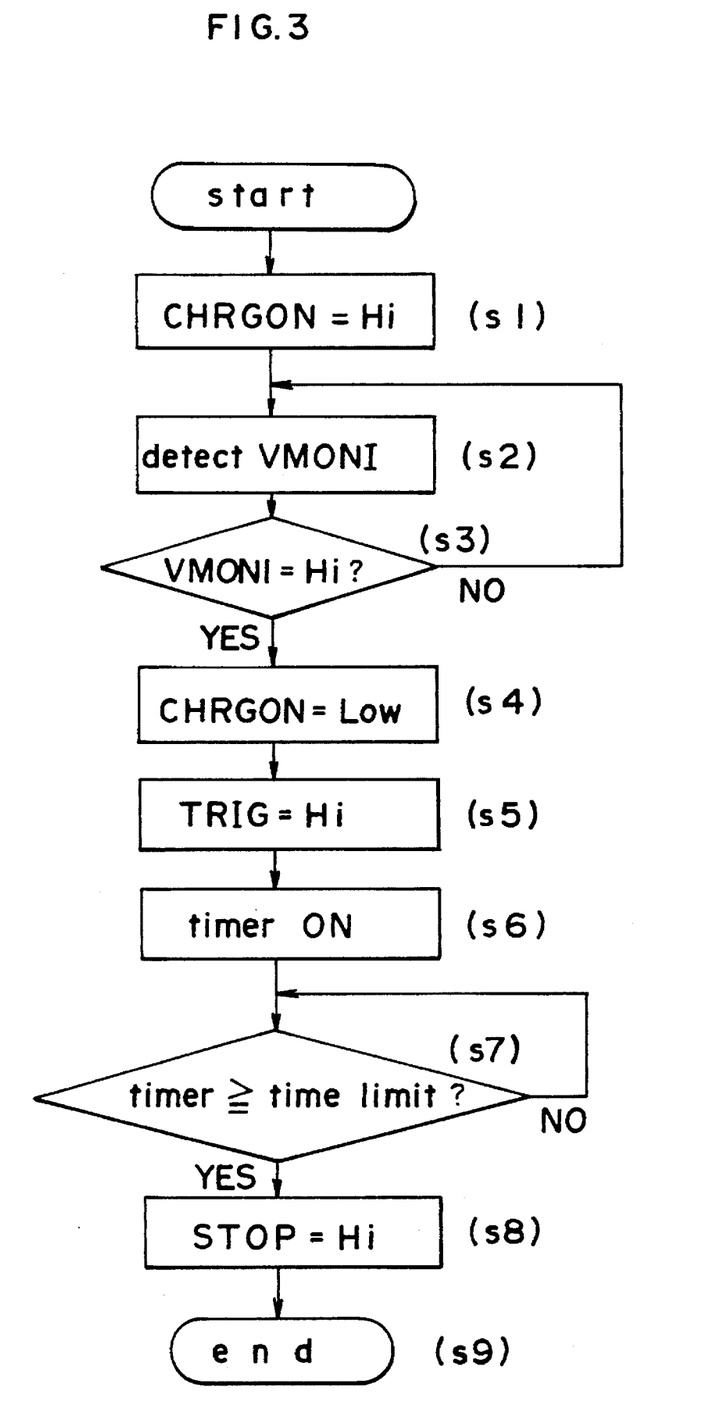
FIG. 3 is a flow chart showing the operational sequence regarding emission of light from the light source.

FIG. 3 is a flow chart showing the operational sequence when light source 1 is caused to emit light, and the light emission operation of the light source is explained below with reference to this drawing. In step S1, signal CHARGEON is set to 'High', and the charge of current in capacitor 15 is begun. Next, signal VMONI is detected in step S2, and it is determined in step S3 whether VMONI is 'High'. Where signal VMONI is 'Low', this indicates that the charged voltage in capacitor 15 is insufficient to cause light source 1 to emit light, and where signal VMONI is 'High', this indicates that the charged voltage in capacitor 15 is sufficient to cause light source 1 to emit light. Where it is determined in step S3 that the charged voltage is sufficient, signal CHARGEON is set to 'Low' in step S4, and charge is completed.

Next, in step S5, by setting signal TRIG to 'High', emission of light from light source 1 is begun, and in step S6 the timer (not shown in the drawings, built into controller 8) for monitoring the duration of light emission is turned ON.

In step S7 the process waits until the timer value reaches the time for termination, and when the time for termination is reached, the emission of light is terminated in step S8 by setting signal STOP to 'High'). Incidentally, this time for termination is set beforehand, and this setting operation is described below.

Figure 4:
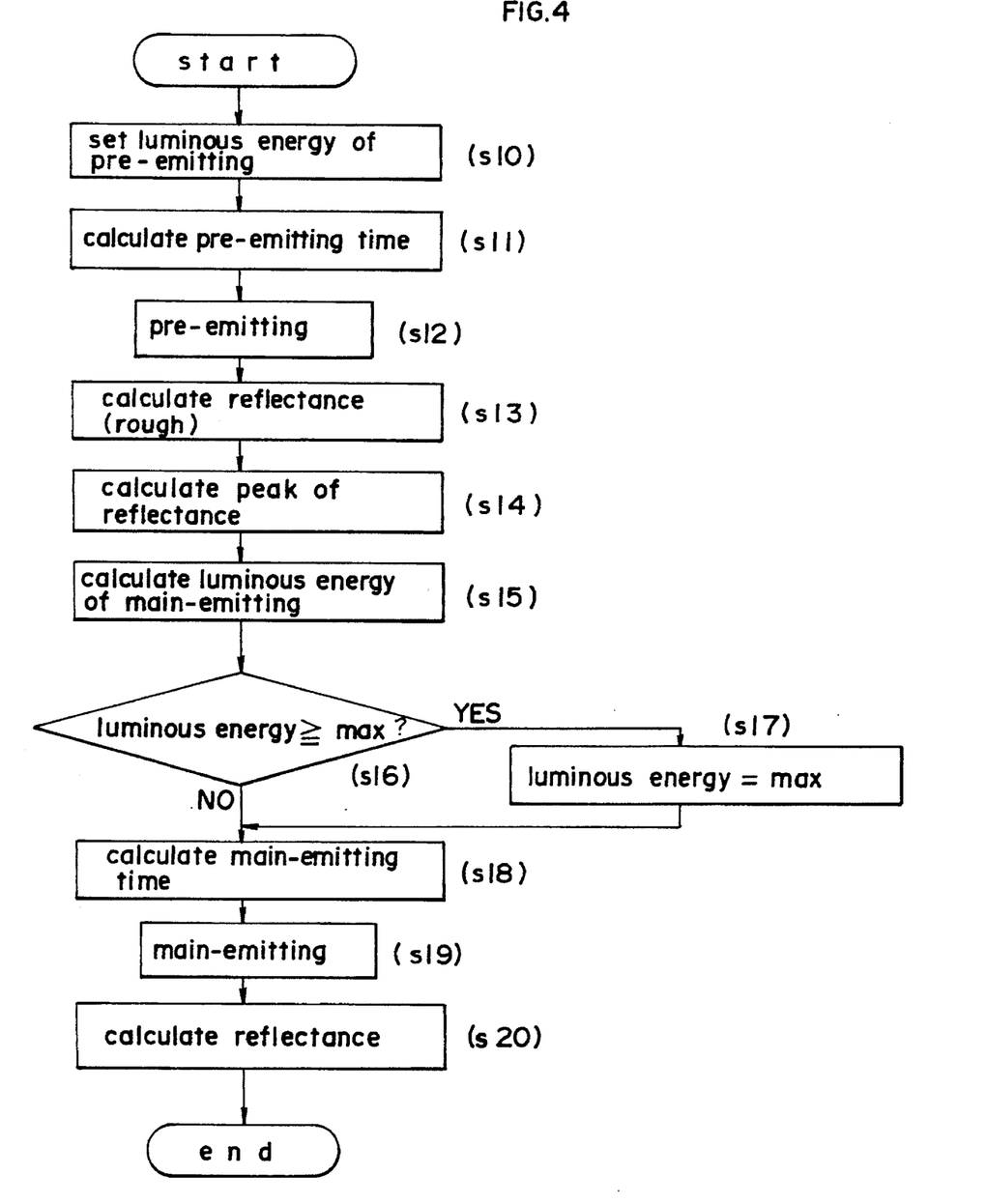
FIG. 4 is a flow chart showing the operational sequence regarding measurement performed by the colorimetric device of this invention.

FIG. 4 is a flow chart showing the operational sequence for color measurement performed by the colorimetric device of this invention. As described above, in this invention, because the luminous energy of the emitted light at the time of measurement is regulated in accordance with the sample's reflectance, it is necessary to have a rough idea of the sample's reflectance beforehand. Therefore, light emission is performed twice in this embodiment. In the first light emission, a luminous energy of the light is emitted at the level such that tile count value does not overflow even if the sample has high reflectance, and the approximate reflectance of the sample is sought from tile obtained count value. The level of the second emission of luminous energy is then determined based on the previously obtained sample reflectance, and color measurement is performed by means of this light emission. Incidentally, the first light emission will be termed the preliminary light emission below, while the second light emission will be termed the main light emission.

First, in the first step, step S10, the luminous energy of the light to be emitted in the preliminary light emission is set. This setting may be saved in a fixed fashion in the device beforehand, or may be performed manually by the user at the time of measurement. In this embodiment, the luminous energy of the light emission during preliminary emission is set at 2% of maximum emission, and is saved in a fixed fashion in the device. Next, in step S11, the amount of time necessary to perform the emission of light of the set luminous energy is calculated. In step S12, light source 1 is caused to emit light (preliminary light emission) for the amount of time calculated above, and in step 13 the reflectance of each wavelength component, i.e., the spectral reflectance, is calculated based on the output from the photoelectric conversion element at this time. In step S14, the peak value of the spectral reflectance calculated in step S13 is calculated, and in step S15 the luminous energy to be emitted for the main light emission is calculated based on this peak reflectance value. In this embodiment, the luminous energy to be emitted for the main light emission when measuring a sample with 100% reflectance is 40% of maximum light emission. In step S16, it is determined whether the luminous energy to be emitted for the main light emission that was calculated in step S15 will not in actuality cause the count value to overflow, and if it will, the process advances to step S17 and the luminous energy to be emitted is set to the maximum permissible amount. In this embodiment, the maximum permissible amount is 90% of maximum light emission.

In step S18, the light emission time necessary in order to perform light emission of the luminous energy of the light previously established is calculated, and the main light emission is carried out in step S19. In step S20, the spectral reflectance of the sample is calculated based on the output from the photoelectric conversion element at the time that the main emission is carried out.

The above comprises the operational sequence for the measurement operation in the colorimetric device of this invention.

Figure 5:
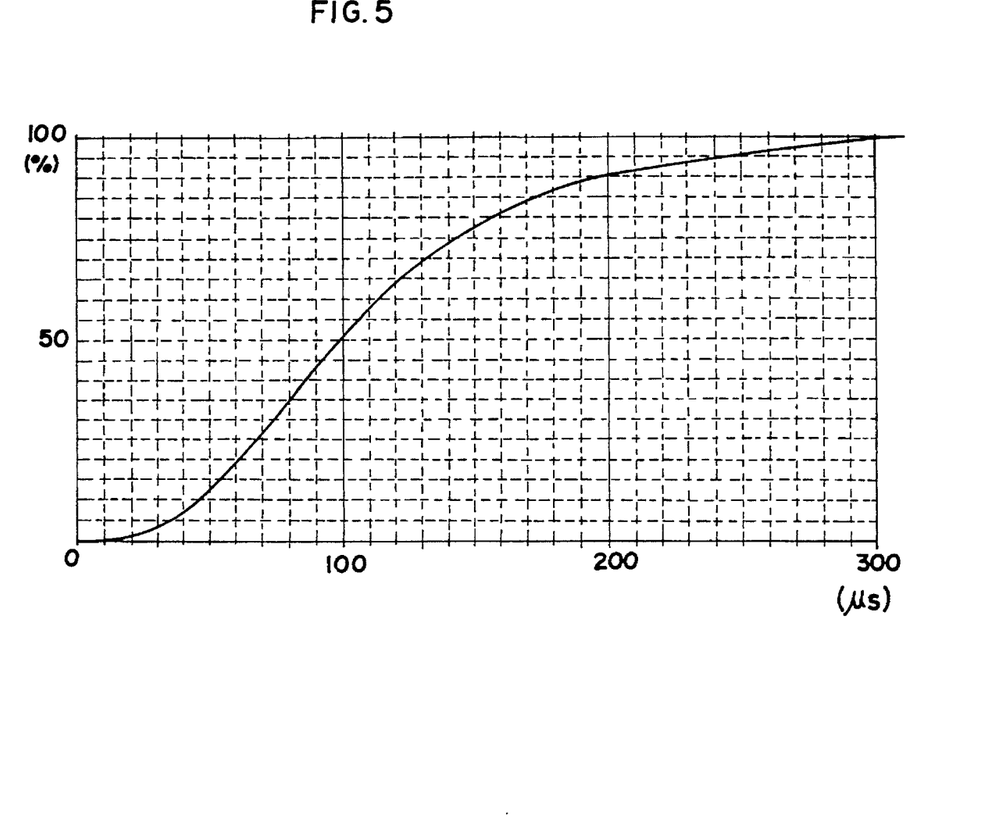
FIG. 5 is a graph showing the relationship between the luminous energy of the light emitted by a xenon lamp light source and the duration of light emission.

FIG. 5 is a graph showing the relationship between the luminous energy emitted by the xenon lamp comprising light source 1 and the duration of light emission. Luminous energy is plotted along the y-axis and the duration of light emission is plotted along the x-axis. The graph was drawn by actually causing the luminous energy to be regulated at 10 μsec intervals, and measuring the count value for each duration, wherein the time at which the count value becomes the maximum is deemed 100%. In this embodiment, the duration of light emission by the light source is calculated based on this graph. Incidentally, the method of calculating the duration of light emission is not limited to this method; a method in which durations of light emission corresponding to each luminous energy are stored in memory as a table is also acceptable.

Incidentally, in the embodiment described above, a device that measures the color of a sample by receiving light reflected off the sample was explained, but the same operation is possible for a device that measures the color of a sample by receiving light passing through the sample. In this case, the construction may be changed such that the light from the sample is led to a measuring unit. In addition, the above embodiment may also be easily applied in a device which measures other optical properties of the sample, such as density.

What is claimed is:

1. An optical properties measuring device comprising:
   a light source that irradiates a measurement sample;
   a photosensor that receives a light from the irradiated measurement sample and outputs an electrical signal in response to an intensity of the light;
   a preliminary light emission means that performs preliminary light emission from the light source prior to a main light emission for sample measurement;
   a preliminary calculating means that approximates optical properties of the sample based on an electrical signal output from the photosensor at a time of preliminary light emission;
   a determining means that determines a luminous energy level for the main light emission for sample measurement based on the optical properties obtained by means of said approximation of the preliminary calculating means;
   a main light emission means that, when the sample is measured, performs main light emission from the light source in accordance with the determined level of luminous energy;
   a main calculating means that calculates optical properties of the sample based on only an electrical signal output from the photosensor at a time of the main light emission; and
   an output means that outputs as sample measurement results the optical properties of the sample calculated by the main calculating means.

2. A device claimed in claim 1, wherein the photosensor receives the light reflected off the sample and wherein said optical properties are reflectances.

3. A device claimed in claim 1, wherein the photosensor receives the light passing through the sample and wherein said optical properties are transmittances.

4. A device claimed in claim 1, further comprising a spectral filter that disperses the light from the irradiated measurement sample into multiple basic wavelength components, wherein said photosensor receives the dispersed light and outputs an electrical signal in accordance with the intensity of each basic wavelength component and wherein said optical properties are spectral properties.

5. A device claimed in claim 1, wherein said determining means has a table in which is stored a relationship between optical properties and luminous energy.

6. A spectral reflectance measuring device comprising:
   a light source that irradiates a measurement sample;
   a spectral filter that disperses a light irradiated to and reflected off the sample into multiple basic wavelength components;
   a photosensor that receives the dispersed light and outputs an electrical signal in response to an intensity of each basic wavelength component;
   a preliminary light emission means that performs preliminary light emission from the light source prior to a main light emission for sample measurements;
   a preliminary calculating means that approximates spectral reflectance of the sample based on an electrical signal output from the photosensor at a time of preliminary light emission;
   a determining means that determines a luminous energy level for the main light emission for sample measurement based on the spectral reflectance obtained by means of said approximation;
   a main light emission means that, when the sample is measured, performs main light emission from the light source in accordance with the determined level of luminous energy;
   a main calculating means that calculates spectral reflectance of the sample based on only an electrical signal output from the photosensor at a time of main light emission; and
   an output means that outputs as sample measurement results the spectral reflectance of the sample calculated by the main calculating means.

7. A device claimed in claim 6, wherein said determining means determines the level of luminous energy so that the higher the spectral reflectance calculated by the preliminary calculating means is, the smaller the luminous energy is.

8. A device claimed in claim 6, further comprising a detection means that detects the maximum value from among the spectral reflectance of each basic wavelength component based on the output from the preliminary calculating means, wherein the above determining means determines the level of luminous energy based on the maximum reflectance value detected by said detection means.

9. A device claimed in claim 6, wherein said preliminary calculating means and main calculating means have a conversion circuit that converts the electrical signal output from the photosensor into a count value proportional to the reflectance of the sample.

10. A device claimed in claim 6, wherein said determining means has a table in which is stored the relationship between sample reflectance and luminous energy.

11. A spectral transmittance measuring device comprising:
    a light source that irradiates a measurement sample;
    a spectral filter that disperses a light irradiated to and passing through the sample into multiple basis wavelength components;
    a photosensor that receives the dispersed light and outputs an electrical signal in response to an intensity of each basic wavelength component;
    a preliminary light emission means that performs preliminary light emission from the light source prior to a main light emission for sample measurement;
    a preliminary calculating means that approximates spectral transmittance of the sample based on an electrical signal output from the photosensor at a time of preliminary light emission;

a determining means that determines a luminous energy level for the main light emission for sample measurement based on the spectral transmittance obtained by means of said approximation.

12. A device claimed in claim 11, wherein said determining means determines the luminous energy level so that the higher the spectral transmittance calculated by the preliminary calculating means is, the smaller the luminous energy is.

13. A device claimed in claim 11, further comprising a detection means that detects the maximum value from among the transmittance of each basic wavelength component based on the output from the preliminary calculating means, wherein said determining means determines the level of luminous energy based on the maximum transmittance value detected by said detection means.

14. A device claimed in claim 11, wherein the said preliminary calculating means and main calculating means have a conversion circuit that converts the electrical signal output from the photosensor into a count value proportional to the transmittance of the sample.

15. A device claimed in claim 11, wherein said determining means has a table in which is stored the relationship between sample transmittance and luminous energy.

16. A colorimetric device comprising:

a light source that irradiates a measurement sample;

a spectral filter that disperses a light irradiated to and reflected off or passing through the sample into multiple basic wavelength components;

a photosensor that receives the dispersed light and outputs an electrical signal in response to an intensity of each basic wavelength component;

a preliminary light emission means that performs preliminary light emission from the light source prior to a main light emission for sample measurement;

a preliminary calculating means that approximates spectral reflectance or spectral transmittance of the sample based on an electrical signal output from the photosensor at a time of preliminary light emission;

a determining means that determines a luminous energy level for the main light emission for sample measurement based on the spectral reflectance or spectral transmittance obtained by means of said approximation;

a main light emission means that, when the sample is measured, performs main light emission from the light source in accordance with the determined level of luminous energy;

a main calculating means that calculates spectral reflectance or spectral transmittance of the sample based on an electrical signal output from the photosensor at a time of main light emission; and an output means that outputs as a sample's measured color value the spectral reflectance or spectral transmittance of the sample calculated by the main calculating means.

17. An optical measuring system for measuring the optical properties of a sample with an improved accuracy of measurement over a measurement range comprising:

a light source for irradiating a measurement sample;

means for driving the light source to provide a first intensity of light and subsequently a second intensity of light which is different than the first intensity of light;

photosensor means for receiving light from the irradiated measurement sample and providing a first output signal representative of the first intensity of light after contact with the measurement sample and a second output signal representative of the second intensity of light after contact with the measurement sample;

determining means responsive to the first output signal from the photosensor means for determining a level of luminous energy to be output from the light source, during the driving of the light source to provide the second intensity of light appropriate for measuring the maximum ratio between a maximum measurable reflectance and a minimum measurable reflectance for the measurement sample and causing the means for driving to provide the second intensity of light representative of the determined level of luminous energy;

calculating means to calculate optical properties of the measurement sample from only the second output signal of the photosensor means; and an output means for providing the results of the calculating means.

18. The optical measuring system of claim 17, wherein the first intensity of light is less than the second intensity of light.

* * * * *